United States Patent [19]

Kunii

[11] Patent Number: 4,681,120
[45] Date of Patent: Jul. 21, 1987

[54] ULTRASONIC DIAGNOSING APPARATUS

[75] Inventor: Yutaka Kunii, Tochigi, Japan

[73] Assignee: Kabushiki Kaisha Toshiba, Kawasaki, Japan

[21] Appl. No.: 696,055

[22] Filed: Jan. 29, 1985

[30] Foreign Application Priority Data

Feb. 3, 1984 [JP] Japan ................................ 59-17092

[51] Int. Cl.⁴ ............................................. A61B 10/00
[52] U.S. Cl. .................................................... 128/660
[58] Field of Search ................................ 128/660–661; 73/620, 625–626, 642–644

[56] References Cited

U.S. PATENT DOCUMENTS

| | | | |
|---|---|---|---|
| 4,059,343 | 11/1977 | Murdock | 73/644 X |
| 4,094,306 | 6/1978 | Kossoff | 128/2 V |
| 4,206,763 | 6/1980 | Pedersen | 128/660 |
| 4,237,901 | 12/1980 | Taenzer | 128/660 |
| 4,252,125 | 2/1981 | Iinuma | 128/660 |
| 4,282,880 | 8/1981 | Gardineer et al. | 128/660 |
| 4,316,271 | 2/1982 | Evert | 128/660 X |
| 4,407,293 | 10/1983 | Suarez, Jr. et al. | 128/660 |
| 4,483,343 | 11/1984 | Beyer et al. | 128/660 |

FOREIGN PATENT DOCUMENTS 3224290 12/1983 Fed. Rep. of Germany ...... 128/660

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

Water is filled in a receptacle, and an ultrasonic-wave transmitting flexible membrane is attached to the receptacle in a watertight manner. An ultrasonic probe is provided in the receptacle for mechanical scanning. The receptacle is coupled with a pipe through which the water in the receptacle can circulate. A pump and a three-way cock are attached to the pipe. A tank containing water is connected to the three-way cock. When the pump is actuated, with the tank and the pipe connected by the three-way cock, the water is introduced from the tank into the receptacle to raise the water pressure. When the receptacle and the tank are connected by the three-way cock, the water escapes from the receptacle into the tank to lower the water pressure in the receptacle. Thus, the water pressure in the receptacle can be adjusted to locate the breast in an optimum position relative to the probe for ultrasonic diagnosis while the breast is supported on the membrane.

12 Claims, 7 Drawing Figures

ULTRASONIC DIAGNOSING APPARATUS

BACKGROUND OF THE INVENTION

The present invention relates to an ultrasonic diagnosing apparatus adapted to diagnosing the diseases of mammary glands and mastocarcinoma.

When ultrasonic waves are applied to a patient, they are reflected by the boundaries between different tissues of the patient. A sectional slice image of an internal organ or abnormal tissue of the patient can be formed from the echoes of the ultrasonic waves. In order to prevent attenuation and reflection of the ultrasonic waves travelling between the patient and a probe which generates and detects the ultrasonic waves, an acoustic coupler is interposed between the probe and the patient. For the acoustic coupler, water is often used because it resembles the patient in ultrasonic-wave propagation characteristics.

FIG. 1 shows a prior art ultrasonic diagnosing apparatus with a receptacle filled with water. A receptacle 10 contains water 2. A patient is held with her breast 4 fitted in an opening 12 of the receptacle 10. A probe 14 is disposed in the receptacle 10 and can be movable in the direction of arrow 6. The probe 14 extends in the direction of arrow 8 (see FIG. 3) perpendicular to the direction of the arrow 6. It has a number of piezoelectric elements 16 arranged in the direction of arrow 8. The elements 16 emit ultrasonic waves toward a region 18 schematically shown in FIG. 3, thereby achieving electronic scanning in the direction of arrow 8. At the same time, the probe 14 moves in the direction of arrow 6, thus performing mechanical scanning. Since the patient's breast 4 directly contacts the water 2, the reflection and attenuation of ultrasonic waves are limited, which results in relatively good sectional slice images. In this prior art apparatus, however, the breast 4 may get wet and foreign matter is liable to enter the water 2. The foreign matter reflects the ultrasonic waves, lowering the image quality. As the patient breathes, her breast moves. This makes it difficult to form an accurate image.

FIG. 2 shows another prior art ultrasonic diagnosing apparatus. This apparatus differs from the apparatus shown in FIG. 1 in that the opening 22 of the receptacle 10 is closed by a membrane 24. The membrane 24 is formed of flexible material having acoustic characteristics similar to those of an organism and can closely contact with the breast 4. The receptacle 10 and the membrane 24 form a vessel. This vessel is filled with water. The breast 4 can be supported by the membrane 24. The depth to which a patient's breast 4 may sink is limited within a range as taken from the ultrasonic probe 14. Thus, the breast 4 is kept relatively flat, pressed onto the membrane 24. Accordingly, when the ultrasonic waves are applied to the breast 4, the direction of incidence of the ultrasonic waves and the surface of the breast 4 define a substantially right angle (incidence angle). As a result, the breast 4 reflects less waves, leading to improved sensitivity, reduced artifacts, and increased depth of visual field.

As shown in FIG. 3, the ultrasonic propagation region, i.e., a specified zone S is narrow since the waves generated by the piezoelectric elements 16 have both a convergent acoustic field and a diffuse acoustic field, whose envelopes have the shape shown in FIG. 3. An ultrasonic diagnosis should preferably be made by using the zone S which is high in ultrasonic density.

Women, as well as men, have breasts of different sizes. Hence, the bottom portion of the breast varies according to the patient although the breast is supported by the membrane 24. The zone S is relatively short in length. Use of a mechanism for adjusting the vertical position of the probe 14 contradicts the requirement for the miniaturization of the ultrasonic diagnosing apparatus. Also, it is very difficult to change the focus point by replacing an acoustic lens in an ultrasonic vibration surface of the probe 14, since the probe 14 is contained in the sealed vessel. Therefore, the region of the breast 4 to be examined by ultrasonic diagnosis may sometimes be off the preferable zone S for the diagnosis. In diagnosing mastocarcinoma, the objective region to be examined is located on that portion of the breast beside the armpit. In this region, however, the contact between the membrane and the breast is loose, so that an air layer is liable to lie between them. Such an air layer makes the ultrasonic diagnosis difficult.

These drawbacks of the prior art ultrasonic diagnosing apparatus are fatal especially in, for example, a group examination in which a number of objects are examined without leaving any substantial chance of reexamination.

SUMMARY OF THE INVENTION

The object of the present invention is to provide an ultrasonic diagnosing apparatus capable of producing distinct and satisfactory sectional slice images despite the variations in size of the breasts to be examined between individuals and adapted for the diagnosis of mastocarcinoma and other diseases.

According to an aspect of the present invention, there is provided an ultrasonic diagnosing apparatus for examining a patient comprising a receptacle containing a liquid acoustic coupling medium and having a substantially horizontal upper surface and an opening provided to said surface, an ultrasonic-wave transmitting flexible membrane attached to the receptacle in a liquid-tight manner so as to cover the opening, a portion of the patient to be examined being put on the membrane, an ultrasonic probe disposed in the liquid in the receptacle for transmitting ultrasonic beams into the patient through the membrane and the medium, and pressure increasing means for increasing the pressure of the liquid in the receptacle.

According to the ultrasonic diagnosing apparatus of the invention, the liquid medium pressure inside the receptacle can be finely adjusted even though the region to be examined is the breast or another part which is flexible and subject to individual differences in size, so that the region to be examined can be located in an optimum position for ultrasonic diagnosis. Since ultrasonic waves generated by the probe have a convergent acoustic field and a diffuse acoustic field, an ultrasonic beam is constricted for higher density in a specific zone remote from the probe. According to the invention, the region to be examined can be positioned in the zone where the ultrasonic beam is constricted without regard to the individual differences between patients. Thus, it is possible to obtain distinct images of good quality. Since the water pressure can be controlled freely, the membrane can be closely fitted on the region to be examined even if the region is the armpit or another part which cannot easily be brought into close contact with the prior art membrane. Thus, satisfactory sectional slice images can be obtained with high stability over a wide range.

DETAILED DESCRIPTION OF THE PREFERRED EMBODIMENTS

Figure 4:
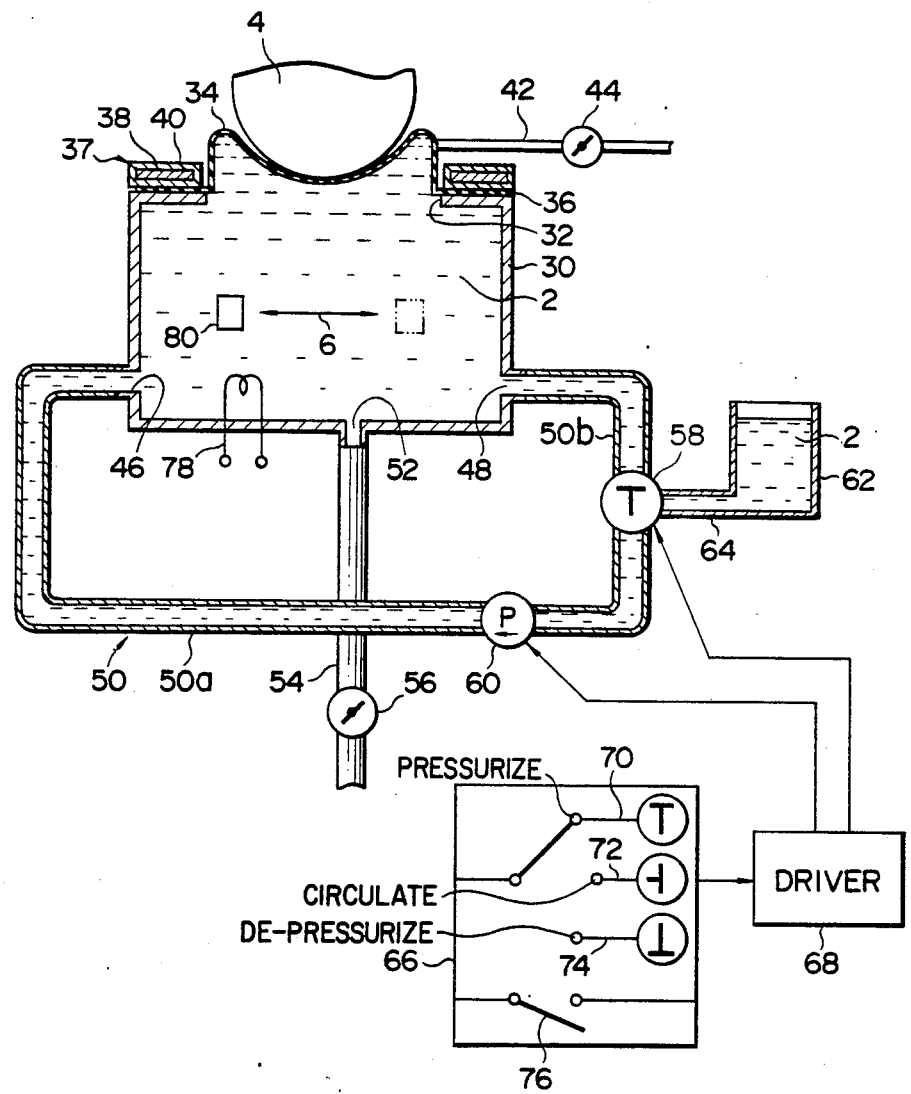
FIG. 4 is a sectional view showing an ultrasonic diagnosing apparatus according to one embodiment of the present invention.
Figure 5:
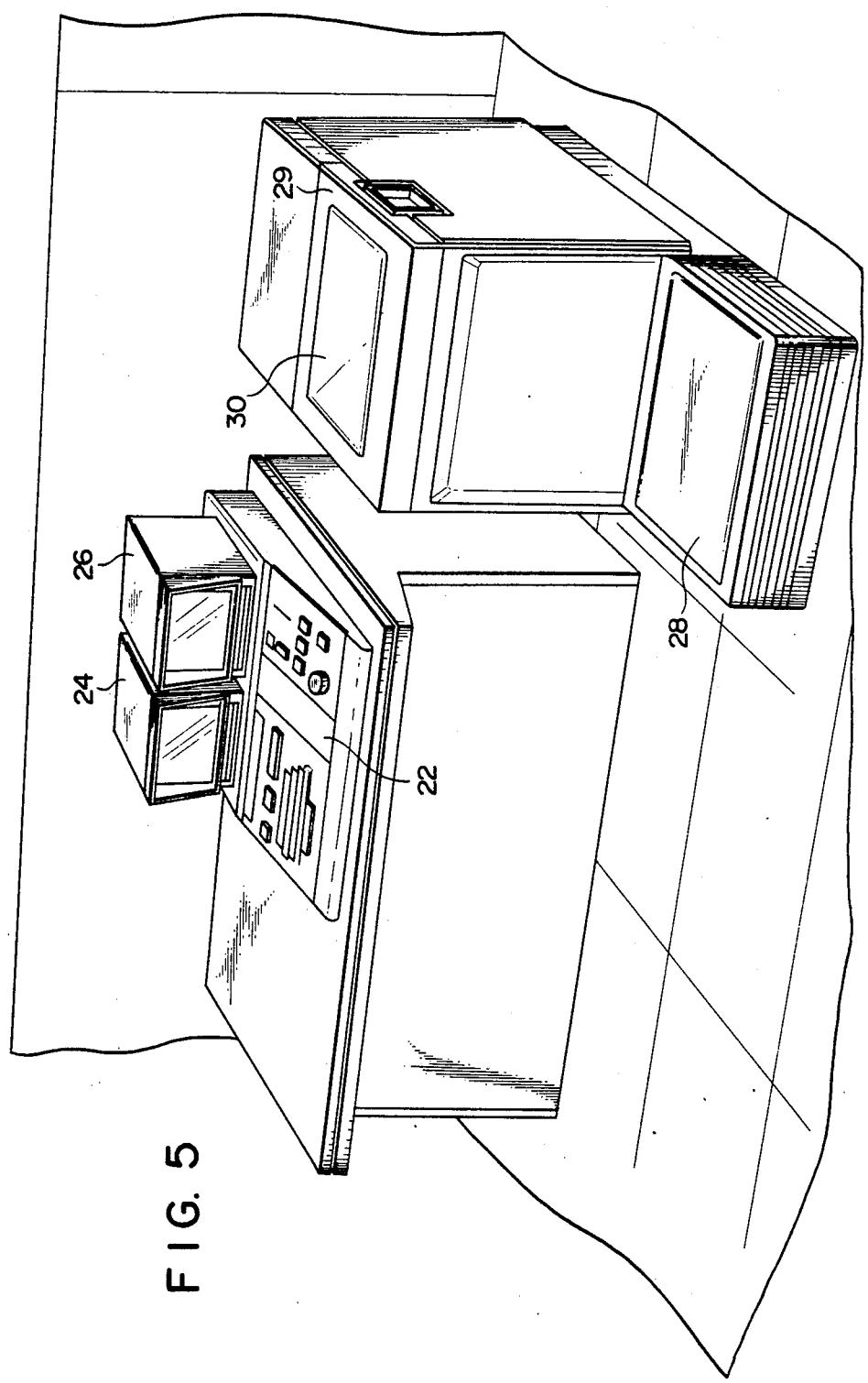
FIG. 5 is a general perspective view of the ultrasonic diagnosing apparatus of FIG. 4.

FIG. 4 shows an ultrasonic diagnosing apparatus using a receptacle according to one embodiment of the present invention, and FIG. 5 is a general perspective view of the apparatus. An operator control panel 22 is mounted on a table which is set on a floor panel of a consultation room. A display 24 for mode C and a display 26 for mode B, for example, are arranged beside the operator control panel 22. A receptacle 30 is set beside the table. A patient is expected to step on a platform 28 in front of the receptacle 30, and to position the breast over the receptacle 30 by bending herself forward.

The receptacle 30 has an opening 32 at the top. A hat-shaped membrane 34 is disposed near the opening 32 so as to close the same. A brim portion 36 at the periphery of the membrane 34 is laid on the top surface of the receptacle 30. A presser member 37 extending along the edge of the opening 32 is placed on the brim portion 36 of the membrane 34. The presser member 37 is fixed to the receptacle 30 so that the brim portion 36 is held between the presser member 37 and the top surface of the receptacle 30. The presser member 37 causes the membrane 34 to be fixed watertight to the receptacle 30. The membrane 34 is formed from a flexible material resembling a living body in acoustic characteristics, e.g., rubber such as silicone rubber. The presser member 37 includes a core plate 38 formed of a steel sheet extending along the peripheral edge of the opening 32 and a cover 40 of a flexible material covering the core plate 38. The cover 40 serves to protect the breast of the patient. The membrane 34 has a hole to which a pipe 42 is connected. A valve 44 is attached to the pipe 42. The valve 44 is normally closed, and air bubbles, if any, in the receptacle 30 can be removed by opening the valve 44.

Two inlet/outlet ports 46 and 48 are formed at the lower end portion of the receptacle 30. A pipe 50 is connected at each end portion to the inlet/outlet ports 46 and 48. Thus, water 2 in the receptacle 30 can circulate through the pipe 50. An exhaust port 52 is bored through the bottom wall of the receptacle 30, and a pipe 54 is connected to the exhaust port 52. A valve 56 is attached to the pipe 54. The valve 56 is normally closed, and the water 2 in the receptacle 30 can be discharged by opening the valve 56.

A three-way cock 58 and a pump 60 are attached to the pipe 50. A tank 62 is connected to the three-way cock 58 by means of a pipe 64. The tank 62 contains the water 2 and is adapted to communicate with the pipe 50 when the three-way cock 58 is shifted. The pump 60 and the cock 58 are driven by a driver 68 in a mode which is selected by a switching unit 66 on the operator control panel 22. The switching unit 66 can set three modes for the operation of the cock 58. In a first mode 70, the tank 62 is connected to a pipe section 50a of the pipe 50 which is fitted with the pump 60, and a pipe section 50b on the side of the inlet/outlet port 48 is cut off from the pipe 64 and the pipe section 50a. In a second mode 72, the pipe sections 50a and 50b are connected, and the pipe 64 is cut off from the pipe sections 50a and 50b. In a third mode 74, the pipe section 50b connects with the pipe 64 so that the water 2 in the receptacle 30 can escape into the tank 62 through the inlet/outlet port 48 and the cross valve 58. The switching unit 66 is provided with a switch 76 for the on-off operation of the pump 60. The driver 68 starts and stops the pump 60 when the switch 76 is turned on and off, respectively.

A heating unit 78 heats the water 2 in the receptacle 30, thereby keeping the water 2 at a temperature near the body temperature.

Figure 6:
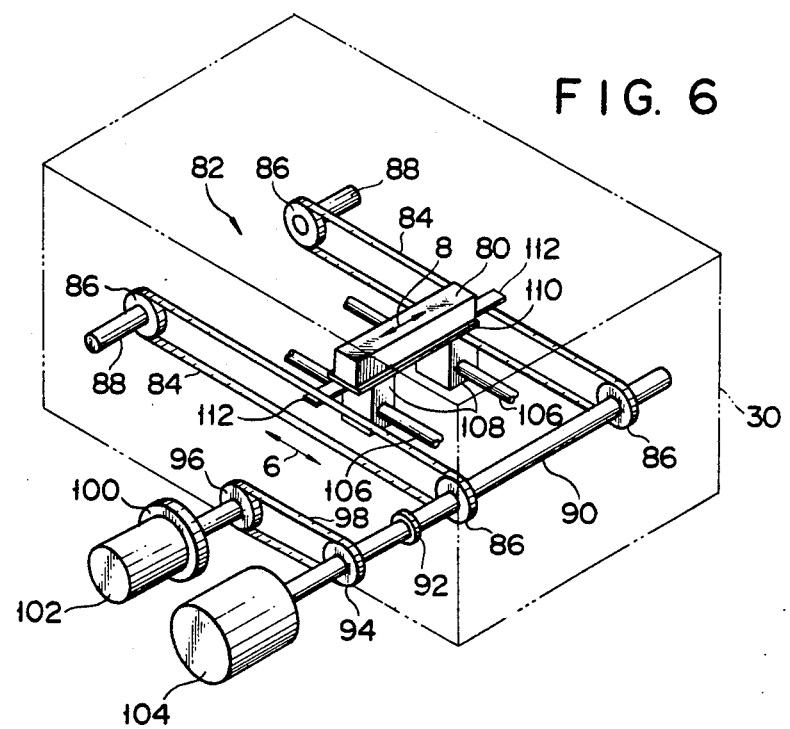
FIG. 6 is a perspective view showing a probe transfer mechanism.

A ultrasonic probe 80 is disposed in the receptacle 30 so as to be movable in the direction indicated by the arrow 6. FIG. 6 shows a transfer mechanism 82 for the probe 80. In FIG. 6, the receptacle 30 is indicated by two-dot chain line, and other members than the transfer mechanism are omitted. Having the same construction as the probe 14 shown in FIG. 3, the probe 80 extends in the direction of the arrow 8 perpendicular to the transfer direction indicated by the arrow 6. A number of piezoelectric elements are arranged along the direction of the arrow 8, and ultrasonic waves are used in electrical scanning in the direction of the arrow 8. A pair of toothed belts 84 extending along the direction of the arrow 6 are each stretched between a pair of toothed pulleys 86. The two pulleys 86 on one side of the arrow 6 are mounted individually on support shafts 88 which are rotatably supported in the receptacle 30 by suitable bearings and the like. The remaining two pulleys 86 on the other side are mounted on a driving shaft 90 which is rotatably supported in the receptacle 30. The position of each support shaft 88 can be adjusted by means of a screw or the like to regulate the tension of its corresponding belt 84.

One end of the driving shaft 90 projects to the outside of the receptacle 30, and a watertight seal member 92 is interposed between the side wall of the receptacle 30 and the driving shaft 90. A toothed driven pulley 94 is mounted on that portion of the shaft 90 outside the receptacle 30, and a rotary encoder 104 for detecting the rotational position of the shaft 90 is attached to the outermost end of the shaft 90. A reduction gear 100 is mounted on the rotating shaft of a motor 102 and a toothed driving pulley 96 on the output shaft of the reduction gear 100. A toothed belt 98 is stretched between the driving pulley 96 and the driven pulley 94. Thus, the rotation of the motor 102 is reduced at a predetermined reduction ratio by the reduction gear 100, and then transmitted to the driving shaft 90 by the belt 98. The position of the shaft 90 is detected by the rotary encoder 104.

A pair of guide shafts 106 extend in the direction of the arrow 6 inside the receptacle 30. A pair of sliding members 108 are fitted individually on the guide shafts 106 so that the former can move along the latter. A mounting base 110 lies fixed on both the sliding members 108 so that the base 110 can move in the direction of the arrow 6 as the sliding members 108 move. The probe 80 is fixed on the base 110 so that its longitudinal direction is in alignment with the direction of the arrow 8. A pair of coupling pieces 112 protrude from the base 110 toward their corresponding belts 84 to be fixed thereto. Thus, the driving shaft 90 reciprocates as the motor 102 rotates alternatingly. As the belts 84 are reciprocated by the alternating rotation of the driving shaft 90, the probe 80 reciprocates in the direction of the arrow 6.

The operation of the ultrasonic diagnosing apparatus with the above construction will now be described. The patient steps on the platform 28 and bends herself forward so that her upper body lies on the housing 29. Thereupon, the breast 4 is supported on the membrane 34. Then, the switching unit 66 is shifted to the first mode 70 so that the pipe 64 connects with the pipe section 50a. At the same time, the switch 76 is turned on to start the pump 60. The water 2 in the tank 62 is forced into the receptacle 30 through the pipe 50 by the pump 60. As a result, the water pressure inside the receptacle 30 increases, so that the breast 4 on the membrane 34 is lifted. If the second mode 72 is selected in the switching unit 66, the pipe sections 50a and 50b connect with each other, so that the water 2 in the receptacle 30 circulates through the pipe 50. Thus, the water pressure inside the receptacle 30 is kept at a fixed level, and the temperature of the water 2 heated by the heating unit 78 becomes uniform.

The ultrasonic probe 80 is driven in the direction of the arrow 6 by the transfer mechanism 82 so that ultrasonic waves generated by the piezoelectric elements of the probe 80 are used for mechanical scanning as well as for the electrical scanning in the direction of the arrow 8. Reflected echoes of the ultrasonic waves are detected by the probe 80 and applied to the input of an image processing apparatus (not shown). These data are image-processed in so-called mode B, and a cross-sectional slice image of the breast parallel to the drawing plane of FIG. 4 is displayed by the display 26.

Figure 1:
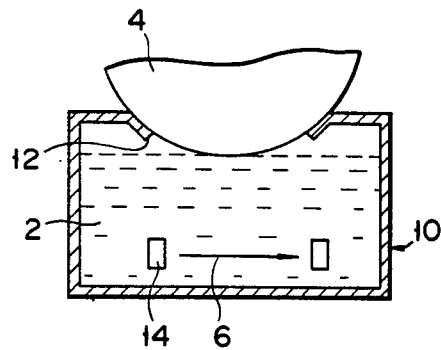
FIGS. 1 and 2 are sectional views schematically showing prior art ultrasonic diagnosing apparatuses.
Figure 2:
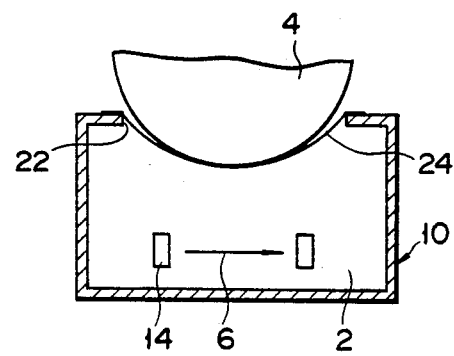
Figure 3:
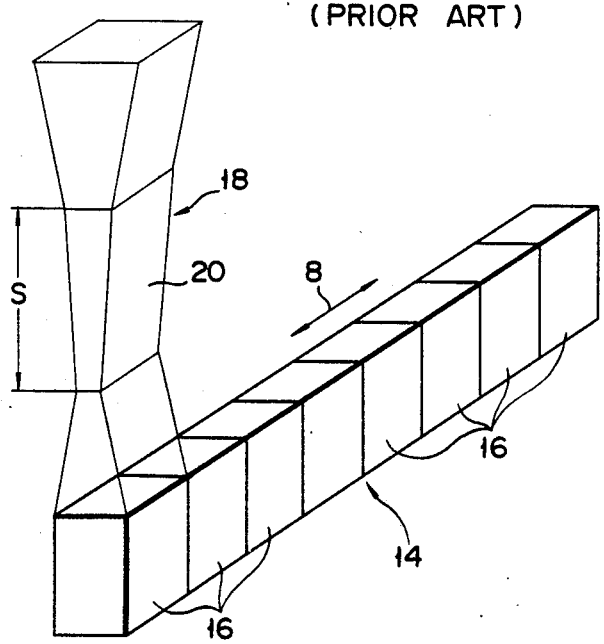
FIG. 3 is a diagram for illustrating an ultrasonic-wave propagation region.

While observing the sectional slice image in mode B, the operator shifts the switching unit 66 between the first to third modes to regulate the water pressure inside the receptacle 30, thereby locating the breast in the optimum position. As shown in FIG. 3, the ultrasonic waves generated from the piezoelectric elements are constricted in zone S. The position of the breast is adjusted so that the cross section of the ultrasonic beam propagation region is narrow and so that the region to be examined is located within zone S with high beam density. Zone S is located at a distance of, e.g., 8 cm to 12 cm from the ultrasonic-wave generating/detecting surface of the piezoelectric elements. Namely, the length of the zone S is about 4 cm. The water pressure inside the receptacle 30 is adjusted so that the breast is positioned within the 4-cm region. If the region to be examine is a specific part subject to, e.g., mastocarcinoma, the operator adjusts the water pressure so that the region is positioned within zone S while observing the sectional slice image in mode B.

Then, the image processing apparatus is switched to so-called mode C, and a vertical-sectional slice image of the breast along a horizontal plane is displayed by the display 24. Zone S is vertically divided into, e.g., 12 parts, and the vertical-sectional slice image of the breast is photographed along each of the 12 horizontal sections. If the breast is fully pressed through the adjustment of the water pressure so that the region to be examined is short, the vertical-sectional slice image of the breast can be obtained at shorter pitches. This leads to an improvement in the accuracy of diagnosis. In the ultrasonic diagnosis in mode C, the switch 76 may be turned off to stop the pump 60.

In lowering the pressure of the water 2 in the receptacle 30, the third mode 74 of the switching unit 66 is selected. In this case, the switch 76 is turned off. Thereupon, the pipe 64 and the pipe section 50b connect with each other, so that the water 2 in the receptacle 30 escapes into the tank 62 by gravity. As a result, the water pressure inside the receptacle 30 is lowered.

If the water pressure inside the receptacle 30 is raised, the breast is strongly forced up by the membrane 34 as the patient rests her weight on the membrane 34 with the breast in contact therewith. Thus, even though the patient breathes, the organ will hardly move, and almost no air will be allowed to come between the breast and the membrane 34.

In diagnosing mastocarcinoma, an image of good quality is preferably obtained by resting the breast 4 on the membrane 34 so as to be closely in contact therewith after increasing the water pressure inside the receptacle 30, and then gradually reducing the water pressure until the armpit region comes into contact with the membrane 34.

The membrane 34 is hat-shaped, projecting upward. With such a shape, the membrane 34 can easily be brought into close contact with a wide-ranging portion of the breast, or another undulating region to be examined, by adjusting the water pressure inside the receptacle 30.

If air bubbles are produced in the receptacle 30, they can be removed by opening the valve 44 and squeezing the membrane 34 so as to guide the bubbles to the pipe 42.

Figure 7:
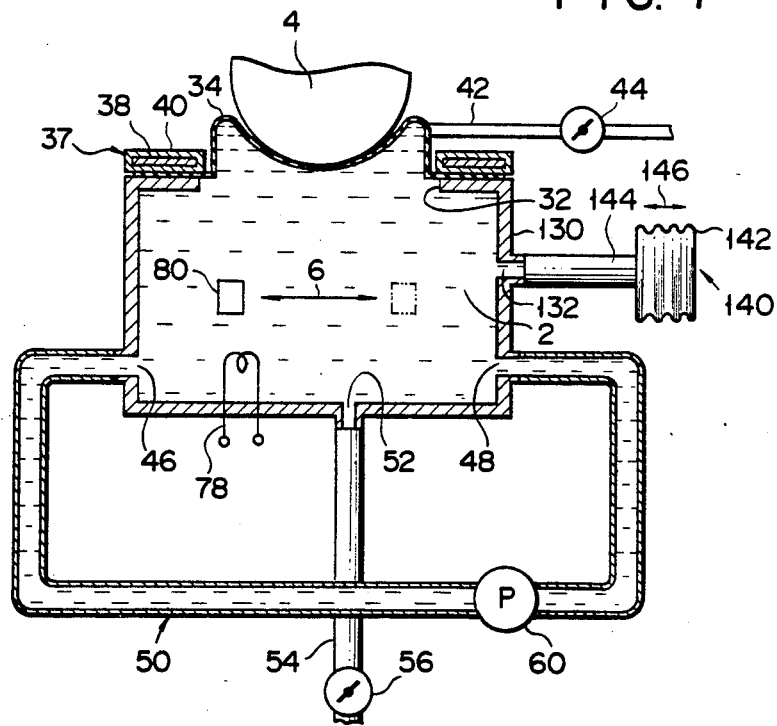
FIG. 7 is a sectional view showing another embodiment of the invention.

Referring now to FIG. 7, another embodiment of the invention will be described. In FIG. 7, like reference numerals are used to designate like portions shown in FIG. 4, and a description of these portions is omitted. A receptacle 130 has an opening 32, inlet/outlet ports 46 and 48, and an exhaust port 52. A membrane 34 is provided at the opening 32, and a circulating pipe 50 with a pump 60 thereon is connected to the inlet/outlet ports 46 and 48. This second embodiment differs from the first embodiment shown in FIG. 4 in that the receptacle 130 is fitted with a bellows-shaped bag pump 140 in place of the cross valve 58 and the tank 62. In this embodiment, therefore, the pump 60 serves not as a water pressurizing means but as a means for circulating the water 2. The bag pump 140 includes a pipe 144 connected to a port 132 formed in the side wall of the receptacle 130 and a bellows member 142 attached to the pipe 144. The water 2 in the receptacle 130 enters the bellows member 142 through the pipe 144, and the water pressure inside the receptacle 130 can be regulated by moving the bellows member 142 in the direction of an arrow 146.

It is to be understood that the present invention is not limited to the above embodiments, and that various changes and modifications may be effected therein by one skilled in the art without departing from the scope or spirit of the invention. More specifically, the apparatus of the invention is not limited to the diagnosis of diseases of the breast, and may also be used for the diagnosis of diseases of other regions.

What is claimed is:

1. An ultrasonic imaging apparatus for providing an image of a patient's breast comprising:
   an impervious receptacle means for containing a liquid acoustic coupling medium, said receptacle means including a port means for accepting and discharging the liquid medium and an opening sized to accept the patient's breast, said port means including two inlet/outlet ports;
   an ultrasonic-wave transmitting, impervious, flexible membrane attached to said receptacle means and covering said opening, said membrane serving to provide a flexible surface upon which the patient's breast is to be laid;
   fixing means for fixing said membrane to said receptacle means in a liquid tight manner;
   an ultrasonic probe means fixed within said receptacle means for transmitting ultrasonic beams into the patient's breast and receiving echos of the ultrasonic beams reflected from the patient's breast through the coupling medium and said membrane;
   tank means for containing the medium;
   pump means for feeding the medium from the tank into the receptacle means and discharging the medium from the receptacle means into said tank means; and
   adjustment means for closely fitting the membrane against the region of the patient's breast to be imaged and selectively varying the distnace between the patient's breast and said probe means by selectively introducing or discharging the liquid medium through said port means and thereby adjusting the pressure of the liquid medium exerted against said flexible membrane; said adjustment means including a pipe connected at each end to the inlet/outlet ports of said port means and a three-way cock attached to the pipe, said tank means being in communication with said three-way cock and said pump being attached to the pipe, said three-way cock adapted to be shifted from a first mode in which the medium in the tank means is fed into the receptacle means by the pump to increase the pressure of the medium in the receptacle means, a second mode in which the medium in the receptacle means is circulated through the pipe by the pump, and a third mode in which the medium in the receptacle means is discharged into the tank to decrease the pressure of the medium in the receptacle means.

2. The ultrasonic imaging apparatus according to claim 1 wherein said membrane is hat-shaped and has its brim portion extending along an edge of the opening of said receptacle means.

3. The ultrasonic imaging apparatus according to claim 2 wherein said fixing means comprises a presser means for pressing the brim portion of said membrane against the receptacle means.

4. The ultrasonic imaging apparatus according to claim 1 wherein said fixing means includes a presser means including a steel core extending along the edge of the opening and a flexible cushion material covering the steel core.

5. The ultrasonic imaging apparatus according to claim 4 wherein said membrane is formed of silicone rubber.

6. The ultrasonic imaging apparatus according to claim 1 further comprising degassing means associated with said membrane for removing air bubbles within the receptacle means.

7. The ultrasonic imaging apparatus according to claim 1 further comprising heating means for heating the medium in the receptacle means.

8. The ultrasonic imaging apparatus according to claim 1 further comprising means for displaying and recording sectional information concerning the patient's breast.

9. The ultrasonic imaging apparatus according to claim 8 wherein said display means displays sectional images of the patient's breast so that an operator can observe the sectional images and operate the adjusting means to adjust the position of the region to be examined with respect to the probe means.

10. The ultrasonic imaging apparatus according to claim 1 further comprising control means coupled with said probe means for causing said probe means to transmit ultrasonic beams that are constricted for higher density in a specific zone remote from said probe means and proxiamte said membrane.

11. The ultrasonic imaging apparatus according to claim 10 wherein said control means is coupled with said adjusting means for causing said adjusting means to position the region of the patient's breast to be examined in the specific zone of said high density beams.

12. The ultrasonic imaging apparatus according to claim 1 further comprising a switch means for selecting the first, second, or third mode of the three-way cock and a driver means coupled with said switch for driving the three-way cock for the mode selected by the switch means.

* * * * *